(12) United States Patent
Richardson (10) Patent No.: US 8,555,732 B2
(45) Date of Patent: Oct. 15, 2013

(54) SUBSTANCE DETECTION DEVICE AND METHOD OF REMOVING BLOCKAGES

(75) Inventor: Stephen Richardson, London (GB)

(73) Assignee: Smiths Detection-Watford Limited, Watford Herts (GB)

( * ) Notice: Subject to any disclaimer, the term of this patent is extended or adjusted under 35 U.S.C. 154(b) by 620 days.

(21) Appl. No.: 12/747,300

(22) PCT Filed: Dec. 11, 2008

(86) PCT No.: PCT/IB2008/003787
§ 371 (c)(1),
(2), (4) Date: Sep. 7, 2010

(87) PCT Pub. No.: WO2009/077862
PCT Pub. Date: Jun. 25, 2009

(65) Prior Publication Data
US 2010/0319463 A1    Dec. 23, 2010

(30) Foreign Application Priority Data

Dec. 11, 2007   (GB) .................................. 0724128.4

(51) Int. Cl.
*G01N 1/20* (2006.01)
(52) U.S. Cl.
USPC ..................................... 73/863.02; 73/863.24
(58) Field of Classification Search
USPC ................. 73/863.02, 863.03, 863.24, 864.34
See application file for complete search history.

(56) References Cited

U.S. PATENT DOCUMENTS

| 3,481,708 | A | | 12/1969 | Isreeli et al. |
| 4,497,214 | A | | 2/1985 | Ramelot |
| 5,425,263 | A | | 6/1995 | Davies et al. |
| 5,760,314 | A | * | 6/1998 | Bromberg et al. .......... 73/863.21 |
| 6,469,781 | B1 | * | 10/2002 | Katz et al. ....................... 356/37 |
| 2002/0078826 | A1 | | 6/2002 | Day |
| 2009/0032695 | A1 | * | 2/2009 | Kaye et al. .................... 250/281 |

FOREIGN PATENT DOCUMENTS

EP    0 447 158 A    9/1991

OTHER PUBLICATIONS

International Search Report for International Application No. PCT/IB2008/003787; mail date Jun. 17, 2009, 3 pages.

* cited by examiner

*Primary Examiner* — Hezron E Williams
*Assistant Examiner* — Rodney T Frank
(74) *Attorney, Agent, or Firm* — Foley & Lardner LLP (57) ABSTRACT

A substance detection device including a chemical substance analyzer, including, a conduit, and a membrane, wherein the membrane extends across a cross-section of the conduit, wherein the membrane is positioned to have one side and an analysis side opposite the one side, wherein the substance detection device is adapted to direct a portion of a chemical substance to the one side through the conduit, the substance detection device further including a particle separation apparatus, including a particle collection device having a collection chamber containing a first fluid and including an outlet, wherein the outlet is in fluid communication with the conduit such that particles directed through the outlet travel through the conduit and chemical substances which may be on those particles directed through the outlet are transferred to the membrane by interacting with the one side of the membrane.

23 Claims, 5 Drawing Sheets

SUBSTANCE DETECTION DEVICE AND METHOD OF REMOVING BLOCKAGES

CROSS-REFERENCE TO RELATED PATENT APPLICATIONS

UK (GB) Priority Patent Application 0724128.4, a United Kingdom patent application filed under the "Applicant(s)/contact point" name of SMITHS DETECTION-WATFORD LIMITED" on Dec. 11, 2007, disclosing apparatus and methods of clearing a blockage, including the specification, drawings, claims and abstract, is incorporated herein by reference in its entirety.

BACKGROUND

Detectors are sometimes used in the field of analytical instruments for detecting chemical substances, including explosive substances and/or nuclear, biological and chemical warfare (NBC) agents.

Apparatuses for and methods of performing an analysis of a chemical substance, including an analysis utilizing ion mobility spectrometry (IMS), are known. Often, these apparatus/methods including parameters which enhance an amount of the chemical substance available for analysis, thus improving the macroscopic sensitivity of the analysis. An increased concentration of substance available for analysis, which can be deposited on a membrane of an ion mobility spectrometer (IMS) system, in turn, increases the macroscopic sensitivity of the analysis by allowing additional sample chemical to pass through the membrane of an IMS system for analysis, due to the additional amounts of sample transferred to the membrane.

Apparatuses for and methods of performing an analysis of a chemical substance often utilize particle separators to separate particles from a gas (such as air). Particles often are collected for analysis using inertial separators, such as cyclones. See, e.g., U.S. Pat. No. 6,508,864. Generally, inertial separators operate by using a combination of forces, such as centrifugal, gravitational, and inertial, to separate particles from the gas in which they are contained. For cyclones, particles generally are separated using centripetal force. Specifically, cyclonic motion causes the particles to separate from the gas and impact a wall of the cyclone that can be wetted with a liquid, such as a suspension buffer. The particles are then removed from the cyclone in a fluid-particle mixture. The particles can exit through an outlet in the chamber and into a conduit extending from the outlet.

Because inertial separators use relatively small volumes of fluid and small diameter fluid conduits (e.g. tubing or other sample collection means), inertial separators, including cyclones, can be prone to blockages. The blockages can be caused by large particles lodged in a conduit or smaller particles aggregating to cause a blockage in a conduit.

Blockages can be removed or prevented by several means. For example, some inertial separators use filters to prevent particles from entering the fluid conduits. Filters capture the particles that are of interest, however, so they cannot simply be excluded, because such exclusion could interfere with the function of the inertial separator. Syringes also can be used to manually remove blockages. For example, an operator uses a syringe to manually inject an amount of fluid into the conduit closest to the chamber of the inertial separator. The fluid dislodges any particles blocking the outlet of the conduit. The dislodged particles can be flushed back out through the sample conduit and dispersed in a larger volume of fluid retained in the inertial separator. Eventually, the particles exit the inertial separator through the outlet and into an analysis device. These methods of preventing and clearing blockages suffer from several limitations. Specifically, filters can hinder the efficient collection of particles. Syringes require an operator to attend to the device and remove blockages when they occur. This is problematic, because inertial separators are often left running unattended for prolonged periods. Thus, blockages go undetected and unresolved because manual injection systems require an operator to detect a blockage and to initiate a blockage clearance procedure.

SUMMARY

Accordingly, there is a need for improved blockage removal devices that can be used, for example, in the field of analytical instruments, including, but not limited to trace detection of chemical, narcotic, explosive, and biological detection. According to a first embodiment of the present invention, there is a substance detection device, comprising, a chemical substance analyzer, including, an ion mobility spectrometer, a desorber, a conduit, and a membrane, wherein the membrane extends across a cross-section of the conduit, wherein the membrane is positioned to have a desorber side in gas communication with the desorber and an analysis side opposite the desorber side, wherein the substance detection device is adapted to direct portion of a chemical substance to the desorber through the conduit so that at least a portion of the entrained chemical substance is transferred to the membrane by interacting with the desorber side of the membrane, wherein the membrane is adapted to diffuse at least a portion of the chemical substance transferred to the membrane through the membrane to the analysis side, and a particle separation apparatus, including a particle collection device having a collection chamber containing a first fluid and including an outlet, wherein the first fluid is a sample fluid containing particles collected by the particle collection device, a first fluid distribution system adapted to direct the first fluid from the particle collection device through the outlet to flow along a first flow path in a first flow direction, a detector adapted to detect a change in a flow rate of the first fluid directed in the first flow direction indicative of a blockage at the first flow path, wherein the apparatus is adapted to automatically direct an unblocking fluid to flow along the first flow path in a second flow direction opposite the first flow direction upon the detection of the change in the flow rate indicative of a blockage at the first flow path to remove the blockage at the first flow path, the chemical interacting with the one side of the membrane, wherein the outlet is in fluid communication with the conduit so that particles directed through the outlet travel through the conduit and substances which may be on those particles directed through the outlet are transferred to the membrane by interacting with the desorber side of the membrane. According to one embodiment, there is provided an apparatus including a flow path for a fluid, a device for detecting a blockage associated with the flow path, a pump arranged to supply fluid such that the fluid flows along a first path in a first direction, and a device for redirecting flow from the pump in response to detection of a blockage so that it flows along the first path in an opposite direction to clear the blockage in the first path. According to another embodiment, there is provided a particle collection system including a particle collection device having an inlet for airborne particles, a fluid inlet, a device for supplying a fluid to the fluid inlet and an outlet for a solution of fluid and particles, a conduit extending from the outlet along which the solution of fluid and particles flows from the outlet in a first direction, a device for extracting the solution of the fluid and particles from the outlet, a device for detecting a blockage to the flow from the outlet, wherein the system is arranged such that detection of a blockage causes a flow of fluid along the conduit in an opposite direction to the outlet to push the blockage out of the outlet.

In some embodiments, the particle collection device preferably includes a cyclone. According to another embodiment, there is provided a cyclone system including a cyclone having an inlet for airborne particles, an inlet for a sample collection solution and outlet for a mixture of sample collection solution and particles, a first pump operable to supply sample collection solution to the sample collection solution inlet, a second pump operable to draw the mixture along a conduit for collection, the second pump being reversible on detection of a blockage to pump fluid back along the conduit to the cyclone inlet, and a switchable connection between the first pump and the conduit so that the first pump is operable on detection of a blockage also to supply sample collection solution to the conduit. Some embodiments may include a separate waste pipe extending from the cyclone to the second pump so that fluid pumped back into the cyclone via its outlet can be removed via the waste pipe.

According to another embodiment, there is a method of automatically removing blockages, including the steps of supplying a fluid to apparatus using a first pump, operating a second pump to draw fluid from the apparatus along a conduit in a first direction, detecting a blockage to flow of fluid along the conduit, reversing the second pump and causing the first pump to supply fluid directly to the conduit so that fluid is caused to flow in the opposite, second direction along the conduit and thereby remove the blockage to flow by the combined effect of the two pumps.

In one embodiment, there is provided an apparatus as disclosed above and/or below, comprising a particle collection device having a collection chamber containing a first fluid and including an outlet, a first fluid distribution system adapted to direct the first fluid from the particle collection device through the outlet to flow along a first flow path in a first flow direction, the first flow path including the outlet, a detector adapted to detect a change in a flow rate of the first fluid directed in the first flow direction indicative of a blockage at the first flow path, wherein the apparatus is adapted to automatically direct unblocking fluid to flow along the first flow path in a second flow direction opposite the first flow direction upon the detection of the change in the flow rate indicative of a blockage at the first flow path to remove the blockage at the first flow path.

In another embodiment, there is an apparatus as disclosed above and/or below, wherein the detector comprises a flow rate meter selected from the group consisting of a variable area flow rate meter, an electromagnetic flow rate meter, a coriolis flow rate meter, a caliometric flow rate meter, a pitot tube flow rate meter, a differential pressure flow rate meter, a thermal conductivity flow rate meter, a vortex shedding flow rate meter, an ultrasonic flow rate meter, a turbine flow rate meter, an optical flow rate meter, and a rotary gear flow rate meter.

In another embodiment, there is an apparatus as disclosed above and/or below, wherein the unblocking fluid comprises the first fluid which has passed through the particle collection device. In another embodiment, there is an apparatus as disclosed above and/or below, wherein the unblocking fluid comprises a sample collection solution that has not passed through the collection chamber of the particle collection device.

In another embodiment, there is an apparatus as disclosed above and/or below, wherein upon the detection of the change in the flow rate indicative of a blockage at the first flow path, the apparatus is adapted to reverse the direction of the first fluid flowing along the first flow path to flow along the first flow path in the second flow direction, the unblocking fluid comprising the first fluid flowing along the first flow path in the second flow direction.

In another embodiment, there is an apparatus as disclosed above and/or below, wherein upon the detection of the change in the flow rate indicative of a blockage at the first flow path, the apparatus is adapted to direct a second fluid to flow along the first flow path in the second flow direction, the unblocking fluid comprising the second fluid flowing along the first flow path in the second flow direction.

In another embodiment, there is an apparatus as disclosed above and/or below, including a particle collection device having a collection chamber containing a first fluid and including an outlet, wherein the first fluid is a sample fluid containing particles collected by the particle collection device, a first fluid distribution system adapted to direct the first fluid from the particle collection device through the outlet to flow along a first flow path in a first flow direction, a detector adapted to detect a change in a flow rate of the first fluid directed in the first flow direction indicative of a blockage at the first flow path, wherein the apparatus is adapted to automatically direct unblocking fluid to flow along the first flow path in a second flow direction opposite the first flow direction upon the detection of the change in the flow rate indicative of a blockage at the first flow path to remove the blockage at the first flow path.

In another embodiment, there is an apparatus as disclosed above and/or below, wherein the detector comprises a flow rate meter selected from the group consisting of a variable area flow rate meter, an electromagnetic flow rate meter, a coriolis flow rate meter, a caliometric flow rate meter, a pitot tube flow rate meter, a differential pressure flow rate meter, a thermal conductivity flow rate meter, a vortex shedding flow rate meter, an ultrasonic flow rate meter, a turbine flow rate meter, an optical flow rate meter, and a rotary gear flow rate meter. In another embodiment, there is an apparatus as disclosed above and/or below, wherein the unblocking fluid comprises the first fluid which has passed through the collection chamber. In another embodiment, there is an apparatus as disclosed above and/or below, wherein the unblocking fluid comprises a sample collection solution that has not passed through the collection chamber of the particle collection device. In another embodiment, there is an apparatus as disclosed above and/or below, wherein upon the detection of the change in the flow rate indicative of a blockage at the first flow path, the apparatus is adapted to reverse the direction of the first fluid flowing along the first flow path to flow along the first flow path in the second flow direction, the unblocking fluid comprising the first fluid flowing along the first flow path in the second flow direction. In another embodiment, there is an apparatus as disclosed above and/or below, wherein upon the detection of the change in the flow rate indicative of a blockage at the first flow path, the apparatus is adapted to direct a second fluid to flow along the first flow path in the second flow direction, the unblocking fluid comprising the second fluid flowing along the first flow path in the second flow direction.

In yet another embodiment, there is an apparatus as disclosed above and/or below, wherein upon the detection of the change in the flow rate indicative of a blockage at the first flow path, the apparatus is adapted to reverse the direction of the first fluid flowing along the first flow path to flow along the first flow path in the second flow direction, the unblocking fluid comprising (i) the first fluid flowing along the first flow path in the second flow direction, and (ii) the second fluid flowing along the first flow path in the second flow direction. In another embodiment, there is an apparatus as disclosed above and/or below, wherein the second fluid comprises a sample collection solution that has not passed through the collection chamber of the particle collection device. In another embodiment, there is an apparatus as disclosed above and/or below, wherein the apparatus includes a sample collection solution supply system adapted to supply sample collection solution to the collection chamber of the particle collection device in an absence of the detection of the change in the flow rate indicative of a blockage at the first flow path, wherein the apparatus is adapted to, upon the detection of the change in the flow rate indicative of a blockage at the first flow path, supply sample collection solution that has not passed through the collection chamber of the particle collection device as the second fluid and direct the second fluid to flow along the first flow path in the second flow direction. In another embodiment, there is an apparatus as disclosed above and/or below, wherein the first fluid distribution system includes a first pump adapted to pump the first fluid flowing along the first flow path in the first direction, the sample collection solution supply system includes a second pump adapted to pump the sample collection solution from a supply of the sample collection solution into the collection chamber of the particle collection device, the apparatus is adapted to reverse a direction of the first fluid flowing through the first pump to pump the first fluid along the first flow path in the second flow direction, the apparatus is adapted to maintain a direction of the sample collection solution flowing through the second pump while directing sample collection solution which has not passed through the collection chamber of the particle collection device to a location, with respect to a partial fluid circuit that includes the outlet and the first pump, between the outlet and the first pump, wherein the sample collection solution that has not passed through the collection chamber of the particle collection device, being the second fluid, combines with the first fluid to form the unblocking fluid and to flow along the first flow path in the second flow direction. In another embodiment, there is an apparatus as disclosed above and/or below, wherein the first fluid distribution system includes a sample pump adapted to operate at a first pump speed to pump the first fluid flowing along the first flow path in the first direction, the sample collection solution supply system includes a buffer supply pump adapted to operate at a variable pump speed to pump the sample collection solution into the particle collection device, the apparatus is adapted to reverse a direction of the first fluid flowing through the sample pump and increase the speed of the sample pump to a second pump speed, to pump the first fluid along the first flow path in the second flow direction, the absolute value of the second pump speed being greater that the absolute value of the first pump speed, the apparatus is adapted to maintain a direction of the sample collection solution flowing through the buffer supply pump while increasing the speed of the buffer supply pump over the variable pump speed while directing sample collection solution that has not passed through the collection chamber of the particle collection device to a location, with respect to a partial fluid circuit that includes the outlet and the first pump, between the outlet and the first pump, wherein the sample collection solution that has not passed through the collection chamber of the particle collection device, as the second fluid, combines with the first fluid to form the unblocking fluid and to flow along the first flow path in the second flow direction.

In another embodiment, there is an apparatus, wherein the apparatus is adapted to determine that the detector has detected a change in the flow rate of the first fluid directed in the first direction indicative of a blockage at the first flow path when at least one of (i) a flow rate of the first fluid flowing in the first flow path decreases by a predetermined regime, and (ii) no movement of the first fluid between two locations in the first flow path is detected. In another embodiment, there is an apparatus as disclosed above and/or below, wherein the apparatus includes a sample dispensing container including an overflow outlet, a supply of the sample collection solution, a waste container, a sample pump, and a sample collection solution supply pump adapted to pump sample collection solution from the supply of the sample collection solution, wherein the first fluid is a sample from the particle collection device which includes particles collected in the particle collection device, wherein the apparatus is adapted to direct, prior to detection of the change in the flow rate indicative of a blockage at the first flow path, the first fluid into the sample dispensing container, and wherein upon the detection of the change in the flow rate indicative of a blockage at the first flow path, the apparatus is adapted to: disconnect the supply of the sample collection solution to the collection chamber of the particle collection device and to connect the supply of the sample collection solution to the first flow path to allow sample collection solution to flow from the supply of the sample collection solution, while bypassing the collection chamber of the particle collection device, to the outlet of the particle collection device; increase a speed of the sample collection solution supply pump adapted to pump sample collection solution from the supply of the sample collection solution; reverse the direction of the sample pump and increasing the speed of the sample pump so that the speed of the sample pump has an absolute value that is greater than an absolute value of the sample pump speed just prior to the detection of the change in the flow rate indicative of a blockage at the first flow path; and pump, using the sample pump operating in the reversed direction and at the increased speed, waste solution from the waste container of the apparatus into the overflow outlet of the sample dispensing container such that sample stored in the sample dispensing container is forced out of the sample dispensing container and flows towards the outlet of the particle collection container so that the first fluid flowing along the first flow path flows along the first flow path in the second flow direction, wherein the first fluid and the second fluid combine to form the unblocking fluid flowing along the first flow path in the second flow direction.

In another embodiment, there is provided a method disclosed comprising, during a first temporal period, obtaining the apparatus of claim 9, the apparatus further including a sample dispensing container including an overflow outlet, a supply of the sample collection solution, a waste container, a sample pump, and a sample collection solution supply pump adapted to pump sample collection solution from the supply of the sample collection solution, wherein the first fluid is a sample from the particle collection device which includes particles collected in the particle collection device; during the first temporal period, directing the first fluid into the sample dispensing container; during the first temporal period, detecting, using the detector, a change in a phenomenon indicative of a blockage at the first flow path; during the first temporal period, disconnecting a supply of the sample collection solution from the particle collection device and connecting the supply of the sample collection solution to the first flow path and directing the sample collection solution to flow from the supply of the sample collection solution while bypassing the collection chamber of the particle collection device to the outlet of the particle collection device; during a second temporal period after the first temporal period, increasing a speed of the sample collection solution supply pump to a speed greater than a speed of the sample collection solution supply pump during the first temporal period to pump sample collection solution from the supply of the sample collection solution; during the second temporal period, reversing the direction of the sample pump from a direction of the sample pump during the first temporal period and increasing the speed of the sample pump so that the speed of the sample pump has an absolute value that is greater than an absolute value of the sample pump speed during the first temporal period; during the second temporal period, pumping, using the sample pump operating at the reversed direction and increased speed, waste solution from the waste container of the apparatus into the overflow outlet of the sample dispensing container, such that sample stored in the sample dispensing container is forced out of the sample dispensing container and flows towards the outlet of the particle collection container so that the first fluid flowing along the first flow path flows along the first flow path in the second flow direction, wherein the first fluid and the second fluid combine to form the unblocking fluid flowing along the first flow path in the second flow direction.

In another embodiment, there is provided a method, wherein the particle collection device is a cyclone separator device, the method further comprising, during the second temporal period, utilizing the sample pump and the sample collection solution supply pump to push a blockage material at the first flow path causing a blockage at the first flow path into the particle collection device such that a volume comprising sample collection solution and blockage material collects in a cyclone chamber of the cyclone separator device.

In another embodiment, there is a method disclosed above and/or below, further comprising: during a third temporal period after the second temporal period, opening a waste outlet connected to the cyclone chamber; during the third temporal period, reversing the direction of the sample pump from the direction of the sample pump during the second temporal period and increasing the speed of the sample pump so that the speed of the sample pump has an absolute value that is greater than an absolute value of the sample pump speed during the second temporal period; and during the third temporal period, sucking the volume from the cyclone chamber through waste outlet to the waste container utilizing a suction generated by the sample pump operating at the reversed direction of the sample pump reversed the second time.

In another embodiment, there is a method disclosed above and/or below, further comprising: during the third temporal period, halting further sample collection solution flow from the supply of the sample collection solution bypassing the collection chamber of the particle collection device to the outlet of the particle collection device; and during the third temporal period, directing the sample collection solution to flow from the supply of the sample collection solution into the sample pump while bypassing the collection chamber of the particle collection device so as to clear material in a flow path extending from the first flow path to at least one of the sample pump, the waste container, and the sample dispensing container.

In another embodiment, there is a method disclosed above and/or below, further comprising: during a third temporal period after the second temporal period, reversing the direction of the sample pump from the direction of the sample pump during the second temporal period and increasing the speed of the sample pump so that the speed of the sample pump has an absolute value that is greater than an absolute value of the sample pump speed during the second temporal period; during the third temporal period, preventing flow through the first flow path in the first flow direction and the second flow direction; and during the third temporal period, directing the sample collection solution to flow from the supply of the sample collection solution into the sample pump while bypassing the collection chamber of the particle collection device while operating the sample collection solution supply pump at the increased speed so as to clear material in a flow path extending from the first flow path to at least one of the sample pump, the waste container, and the sample dispensing container.

In another embodiment, there is a method disclosed above and/or below, further comprising: during a fourth temporal period after the third temporal period, re-enabling flow through the first flow path in the first flow direction and the second flow direction; during the fourth temporal period, increasing the speed of the sample pump above the speed of the sample pump during the third temporal period; and during the fourth temporal period, halting the sample collection solution from flowing from the supply of the sample collection solution into the sample pump while bypassing the collection chamber of the particle collection device, and operating the sample collection solution supply pump at the increased speed so as to flush the volume from the cyclone chamber through the outlet to the waste container.

In another embodiment, there is an apparatus disclosed above and/or below, comprising a particle collection device containing a first fluid and including an outlet, a first fluid distribution system adapted to direct the first fluid from the particle collection device through the outlet to flow along a first flow path in a first flow direction, the first flow path including the outlet, a detector adapted to detect a change in a flow rate of the first fluid directed in the first flow direction indicative of a blockage at the first flow path, and an unblocking means for automatically unblocking a blockage at the first flow path.

In another embodiment, there is provided a method disclosed above and/or below, comprising: during a first temporal period, collecting particles utilizing a cyclone particle collector in a first fluid, the first fluid being located in a collection chamber of the cyclone particle collector including an outlet; during the first temporal period, directing the first fluid through the outlet to flow along a first flow path in a first flow direction, the first flow path including the outlet; during the first temporal period, automatically detecting a change in a flow rate of the first fluid directed in the first flow direction indicative of a blockage at the first flow path; during a second temporal period after the first temporal period, automatically direct unblocking fluid to flow along the first flow path in a second flow direction opposite the first flow direction upon the detection of the change in the flow rate indicative of a blockage at the first flow path to remove the blockage at the first flow path; and during a third temporal period after the second temporal period, automatically directing the first fluid through the outlet to flow along the first flow path in the first flow direction.

In another embodiment, there is an apparatus comprising a particle collection device containing a first fluid and including an outlet, a first pump adapted to pump the first fluid from the particle collection device through the outlet in a first direction along a first flow path in fluid communication with the outlet, a detector adapted to detect a change in a flow rate of the first fluid pumped in the first direction from the outlet indicative of a blockage at the first flow path, wherein the apparatus is adapted to change the direction along the first flow path of the first fluid upon the detection of the change in the flow rate indicative of a blockage at the first flow path.

In another embodiment, there is an apparatus including a blockage clearing apparatus, comprising a second pump for pumping a second fluid from an outlet; a detector for detecting a blockage in the outlet, and wherein upon detection of the blockage, the second pump reverses direction such that the second fluid moves along a first path in a second direction to push the blockage out of the outlet.

In another embodiment, there is an apparatus, wherein the detector comprises a flow rate meter selected from the group consisting of a variable area flow rate meter, an electromagnetic flow rate meter, a coriolis flow rate meter, a caliometric flow rate meter, a pitot tube flow rate meter, a differential pressure flow rate meter, a thermal conductivity flow rate meter, a vortex shedding flow rate meter, an ultrasonic flow rate meter, a turbine flow rate meter, an optical flow rate meter, and a rotary gear flow rate meter.

In another embodiment, there is an apparatus wherein the flow rate meter of the detector comprises at least a first sensor and a second sensor. In another embodiment, there is an apparatus wherein the second fluid comprises a sample particle and a first fluid. In another embodiment as disclosed above and/or below, there is an apparatus wherein the second direction is a direction opposite that of a first direction.

In another embodiment as disclosed above and/or below, there is an apparatus wherein the first sensor and the second sensor comprise a bubble sensor, the first sensor and the second sensor are configured to determine a flow rate, and the flow rate is a function of the time it takes a bubble to move from the first sensor to the second sensor.

In another embodiment, there is an apparatus wherein the blockage exists if the flow rate decreases to a value at or below a predetermined value.

In another embodiment, there is an apparatus wherein the blockage exists if there is no measurable flow rate for at least 10 seconds.

According to another embodiment, there is an apparatus, wherein the apparatus is a particle collection system comprising a particle collection device, wherein the particle collection device comprises a particle inlet for receiving particles, a fluid inlet for receiving a fluid, and an outlet for receiving a second fluid; a first pump for pumping the fluid to the fluid inlet such that the fluid moves along a first path in a first direction, a first conduit for receiving the second fluid from an outlet; a second pump for pumping the second fluid from the outlet; and a detector for detecting a blockage at the outlet; wherein upon detection of the blockage, the second pump reverses direction and the first pump supplies fluid to the first conduit such that the second fluid moves along the first path in a second direction to push the blockage out of the outlet.

In another embodiment, there is an apparatus, wherein the second fluid comprises a sample particle and the fluid. In another embodiment, there is an apparatus wherein the speed of the first pump increases when the detector detects the blockage, the speed of the second pump increases when the detector detects the blockage, or the speed of both the first and second pumps increase when the detector detects the blockage. In another embodiment, there is an apparatus as disclosed above and/or below wherein the sample particle collection device comprises a cyclone.

In another embodiment, there is an apparatus as disclosed above and/or below wherein the first pump operates the fluid to the fluid inlet of a first valve. In another embodiment, there is an apparatus as disclosed above and/or below, wherein the first valve connects to a second conduit, wherein the second conduit connects to a needle, and wherein the needle projects into the particle inlet.

In another embodiment, there is an apparatus as disclosed above and/or below, wherein the cyclone comprises a and wherein the cyclone connects to an impeller or a blower.

In another embodiment, there is an apparatus wherein the chamber comprises a first portion and a second portion and wherein the first portion is closed.

In another embodiment, there is an apparatus further comprising a sixth conduit, wherein the fluid pumped into the cyclone through the outlet travels through the sixth conduit.

In another embodiment, there is an apparatus wherein the fluid travelling through the sixth conduit enters the waste conduit, and wherein the waste conduit extends to a second container.

In another embodiment, there is an apparatus wherein a volume enters the particle detection device when the blockage enters the particle collection device. In another embodiment, there is an apparatus wherein the second pump reverses direction so that the volume in the particle collection device is forced into the second container.

According to another embodiment, there is a method as disclosed above and/or below, wherein the method removes blockages, comprising supplying a fluid to a blockage clearing apparatus using a first pump; operating a second pump to draw the fluid from the blockage clearing apparatus along a conduit in a first direction; and reversing the second pump and causing the first pump to supply the fluid directly to the conduit, wherein the fluid moves in a second direction such that removal of the blockage occurs It is to be understood that both the foregoing general description and the following detailed description are exemplary and explanatory only and are not restrictive of the embodiments as claimed.

BRIEF DESCRIPTION OF THE DRAWINGS

The accompanying drawings, which are incorporated in and constitute a part of this specification, illustrate different embodiments and, together with the description, serve to describe exemplary embodiments.

DETAILED DESCRIPTION

Unless otherwise specified, "a" can refer to one or more. For example, "a outlet" can refer to "one or more outlets" unless otherwise specified.

Unless otherwise specified, the description of one or more components does not preclude additional components. For example, the description of an apparatus including A, B, and C includes an apparatus including A, B, C, and D.

Unless otherwise specified, "and" and "or" are used interchangeably. For example, a device having "A or B" can have both "A" and "B," and a device having "A and B" can have only "A" or "B."

As used herein, "particle collection device" refers to any device used to collect sample particles. Inertial separators are one type of particle collection device. Settling chambers, baffle chambers, and centrifugal collectors (also known as cyclones) are examples of some inertial separators. Cyclones can be single-cyclone separators or multiple-cyclone separators.

Reference will now be made in detail to embodiments, examples of which are illustrated in the accompanying drawings. An effort has been made to use the same reference numbers throughout the drawings to refer to the same or like parts.

Figure 1:
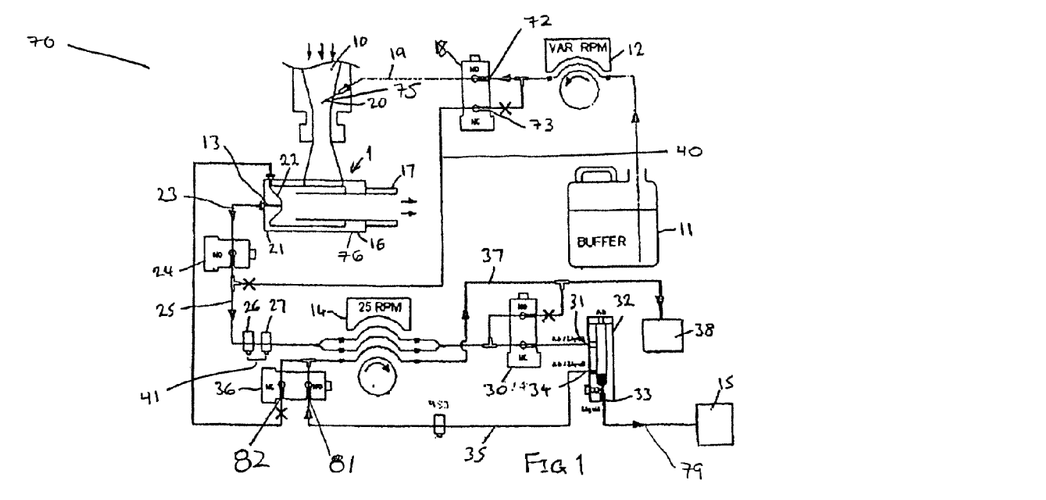
FIG. 1 is a schematic of the particle collection system before a blockage occurs.
Figure 2:
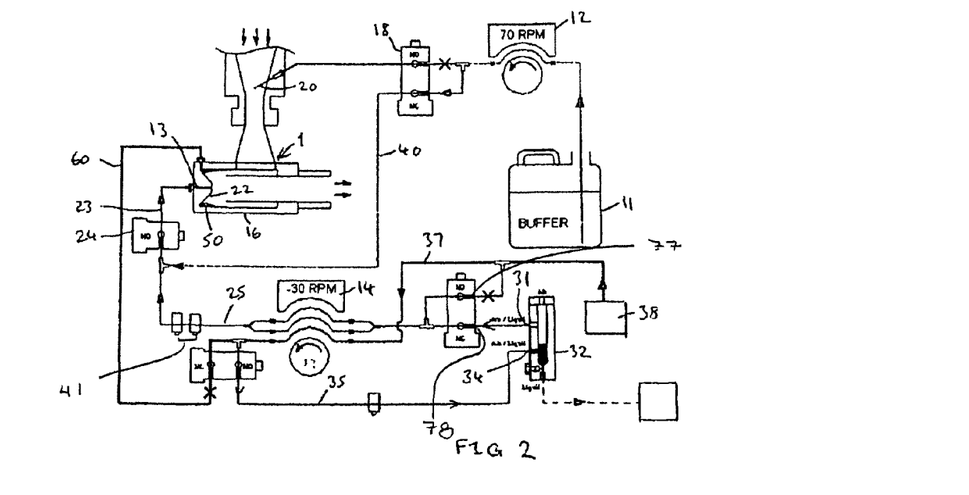
FIG. 2 is a schematic of the particle collection system at a preliminary stage of blockage clearance.
Figure 3:
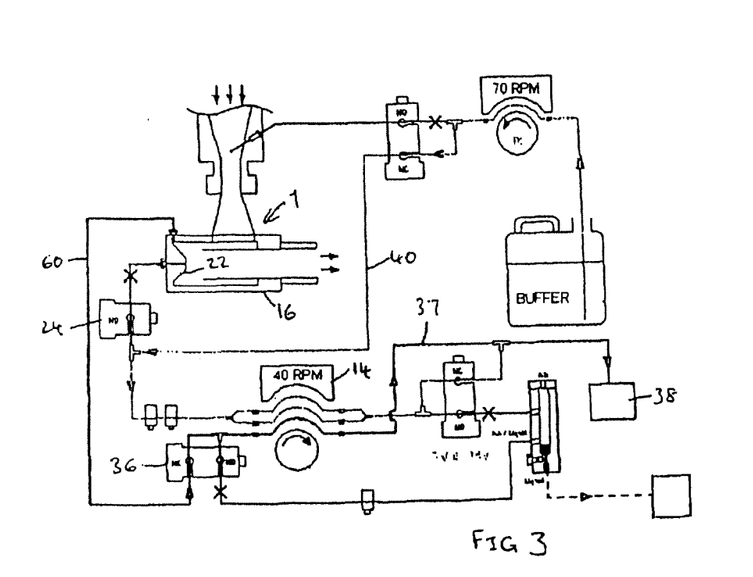
FIG. 3 is a schematic of the particle collection system at a later stage of blockage clearance.

According to a first embodiment, examples of which are shown in FIGS. 1, 2, and 3, a particle collection system 70 comprises a particle collection device 1, a first pump 12, a first conduit 23, a second pump 14, and a detector 41.

As shown in FIG. 1, the particle collection device 1 can include a fluid inlet 75, a particle inlet 10, and an outlet 14. The particle inlet 10 receives particles. The particle collection device 1 can be any particle collection device, such as a cyclone. The cyclone can be connected to a blower or impeller at the particle inlet 10 or at a first outlet 17 so that air is drawn into the cyclone.

The fluid that enters the fluid inlet 75 can be pumped by the first pump 12 to the fluid inlet 75. Alternatively, the fluid can enter the fluid inlet 75 without the aid of the first pump 12. The first pump 12 can pump fluid in a first direction or a second direction. When no blockage is detected, the first pump 12 operates in the first direction along a first path. The first pump 12 can operate at any suitable speed. For example, the first pump can operate at any speed above 0 rpm. In one embodiment the pump can operate at a speed from 20-200 rpm. In another embodiment, the pump can operate at a speed below 70 rpm. The second direction is opposite the first direction. The first pump 12 can be any pump, such as, for example and without limitation, a rotary, bellows, peristaltic, centrifugal, diaphragm, impeller gear. In one embodiment, the pump can be a rotary pump such that the first direction corresponds to clockwise movement, and the second direction corresponds to counterclockwise movement, for example.

The first pump 12 can connect to a first two-way valve 18. A first port 72 of the first two-way valve 18 can connect to a first conduit 19, and a second port 73 of the first two-way valve 18 can connect to a second conduit 40. The first port 72 of the first two-way valve 18 can be open, and the second port 73 of the first two-way valve 18 can be closed.

The first conduit 19 can be any suitable shape, including cylindrical. The first conduit 19 can connect to a needle 20 and a third container 11. The needle 20 can project into the particle inlet 10 so that the contents of the needle 20 enter the collection chamber ("chamber") 16 with the particles or any airborne particles. The third container 11 contains a fluid, such as a sample collection solution. Thus, the needle 20 can be used to provide a fluid, such as a sample collection solution, from the third container 11 to the chamber 16.

The chamber 16 can contain a particle inlet 10. The particle inlet 10 can be oriented in a direction tangential to the chamber 16 so that air is given a swirling motion about the axis of the chamber 16. In some embodiments, the chamber 16 is oriented horizontally. Other orientations, however, of the chamber 16 are possible. For example, the chamber 16 can be oriented vertically or at an angle to the particle inlet 10. The chamber 16 can be any suitable shape, including cylindrical.

The chamber 16 can have a first portion 21 and a second portion 76. In some embodiments, the first portion 21 is closed. The first portion 21 can have a formation 22 that projects from the closed end of the first portion 21 and into the inside of the chamber 16. The top of the formation 22 can include an outlet 13. A wide range of diameters are possible for the outlet 13. For example, the diameter can be less than about 0.2 mm, less than about 0.4 mm, less than about 0.6 mm, less than about 0.8 mm, less than about 1 mm, or less than about 5 mm. In an embodiment, the diameter of the outlet 13 can be about 0.8 mm. The formation 22 can be any suitable shape. For example, the formation 22 can be conical or cylindrical.

The outlet 13 can connect to a third conduit 23. The third conduit 23 can be any suitable shape, such as cylindrical. A wide range of diameters are possible for the outlet 13. For example, the diameter can be less than about 0.2 mm, less than about 0.5 mm, or less than about 1 mm. The third conduit 23 can connect to a second two-way valve 24. The second two-way valve 24 can connect to a fourth conduit 25. The fourth conduit 25 can be cylindrical. The fourth conduit 25 can connect to a second pump 14.

A detector 41 for detecting blockages can be located along the fourth conduit 25. Other locations for the detector 41 are also possible. For example, the detector 41 can be located along any of the other conduits described in this application. The location of the detector 41 is not important, so long as the detector 41 is able to detect blockages. The detector 41 can detect blockages in any way. For example, blockages can be detected based on a change in the rate of fluid flow, a change in pressure, or an optical change.

The second pump 14 can pump a second fluid from the outlet 13 along the fourth conduit 25. When there is no blockage, the second pump 14 can pump in a direction opposite the direction that the first pump 12 operates. In some embodiments, the second pump 14 pumps in the second direction. The second pump 14 can operate at any suitable speed, such as, for example, above 0 rpm. In one embodiment the pump can operate below 200 rpm, In another embodiment the pump can operate at or below 25 rpm. Generally, the second fluid comprises particles and fluid, such as one or more buffers.

The second pump 14 can connect to a third two-way valve 30. The third two-way valve 30 can have a first port 77 and a second port 78. The first port 77 of the third two-way valve 30 can connect to a waste conduit 37. The second port 78 of the third two-way valve 30 can connect to a first container 32 (sample dispensing container). The first port 77 of the third two-way valve 30 can be closed, and the second port 78 of the third two-way valve 30 can be open.

The waste conduit 37 can connect to the second pump 14 and a second container 38. The second pump 14 can pump any waste fluid through the waste conduit 37 to the second container 38. The waste conduit 37 can be any suitable shape, including cylindrical.

The first container 32 can have a container inlet 31, a container outlet 33, and an overflow outlet 34. The container inlet 31 and the container outlet 33 can be located anywhere along the container 32. For example, as shown in FIG. 1, the overflow outlet 34 can be located between the container inlet 31 and the container outlet 33. The second fluid can enter the first container 32 through the container inlet 31 and exit the first container 32 through the container outlet 32. The container outlet 32 empties into an analysis unit 15. The container outlet 32 can directly connect to the analysis unit 15. The container outlet 32 also can empty into a seventh conduit 79 that empties into the analysis unit 15. The seventh conduit 79 can be any suitable shape, including cylindrical. According to one embodiment, as shown in FIGS. 1, 2, and 3 the overflow outlet 34 is located between the container inlet 31 and the container outlet 33, so that if fluid should enter the first container 32 at a higher rate than is discharged through the container outlet 33, it would flow out of the overflow outlet 34.

The overflow outlet 33 can connect to a fifth conduit 35. The fifth conduit 35 can connect the overflow outlet 33 to a fourth two-way valve 36. The fifth conduit 35 can be any suitable shape, including cylindrical. The fourth two-way valve 36 can have a first port 81 and a second port 82. The first port 81 of the fourth two-way valve 36 can be open. The second port 82 of the fourth two-way valve 36 can be closed. The fifth conduit 35 can connect to a waste conduit 37 and extends via the second pump 14 so that the waste fluid is pumped into the second container 38. In normal operation, therefore, the fluid containing the collected particles in suspension is drawn from the particle collection device 1 to the analysis unit 15 for detection and analysis.

Any suitable flow rate metering mechanisms can be used. For example, a variable area flow rate meter, an electromagnetic flow rate meter, a coriolis flow rate meter, a caliometric flow rate meter, a pitot tube flow rate meter, a differential pressure flow rate meter, a thermal conductivity flow rate meter, a vortex shedding flow rate meter, an ultrasonic flow rate meter, a turbine flow rate meter, an optical flow rate meter, and a rotary gear flow rate meter. The detector 41 of the particle collection system 70 can include any amount of sensors. For example, the detector 41 of the particle collection system 70 can include a first sensor 26 or a first sensor 26 and a second sensor 27. Any suitable sensor mechanism can be used. For example, a bubble sensor, a temperature or heat sensor, an electromagnetic sensor, a mechanical-type sensor, a chemical proportion sensor, an odor sensor, an optical radiation-type sensor, an ionizing radiation-type sensor, a non initialized-type sensor, or an initialized system sensor.

According to one embodiment, the detector 41 includes a first sensor 26 and a second sensor 27. The first sensor 26 and the second sensor 27 can determine the flow rate of the second fluid along a conduit, such as the fourth conduit 25. According to one embodiment, the first sensor 26 and the second sensor 27 are bubble sensors. Using bubble sensors, the time elapsed between detection of a bubble between a first sensor 26 and second sensor 27 is measured. The first and second sensors 26, 27 are a known distance apart and the flow rate is a function of the elapsed time and the distance between the first and second sensors 26, 27. Deviation from an expected flow rate can indicate a blockage. A flow rate below a predetermined value can indicate that there is a blockage. A flow rate that is less than 90%, 80%, 70%, 60%, 50%, 40% 30%, 20% or 10% of a predetermined value can indicate that there is a blockage. In one embodiment, a flow rate can be derived from the amount of time that elapses between detection of a bubble between a first sensor 26 and second sensor 27 and an amount of time that increases above, for example 110%, 120%, 130%, 140%, 150% or 175% can indicate that there is a blockage. The failure to detect flow rate for a predetermined time also can indicate a blockage. For example, the failure to detect a flow rate for greater than or equal to 10 seconds can indicate that there is a blockage. In some embodiments, the absence of a flow rate for greater than or equal to 2 seconds, 5 seconds, 15 seconds, or 30 seconds can indicate a blockage.

FIG. 2 shows an exemplary particle collection system 70 after detection of a blockage. Upon detection of a blockage, the speed of the first pump 12 and the second pump 14 increases, the first two-way valve 18 switches, and the second pump 14 operates in the first direction. In some embodiments, the speed of the first pump 12 increases by a factor of at least 1.25, 1.5, 2, or 3. For example, the speed of the first pump 12 can increase to greater than or equal to 70 rpm. When the first pump 12 reaches the increased speed, the first pump 12 can be controlled to provide a substantially constant outlet compensated for varying environmental conditions. In some embodiments, the speed of the second pump 14 can increase by a factor of at least 1.25, 1.5, 2, or 3. For example, the speed of the second pump 14 can increase to greater than or equal to 30 rpm.

When the first two-way valve 18 switches, the first port 72 of the first two-way valve 18 can be closed and the second port 73 of the first two-way valve 18 can be open. Initially, the second port 82 of the fourth two-way valve 36 can remain open.

The closure of the first port 72 of the first two-way valve 18 can disconnect the first pump 12 from the needle 20. When the second port 73 of the first two-way valve 18 opens, the fluid from the third container 11 can move from the first pump 12 into the second conduit 40, through the second conduit 40 to the second two-way valve 24, and from the second two-way valve 24 to the outlet 13.

When the second pump 14 operates in the first direction, the second pump 14 can pump waste fluid from the second container 38 through the waste conduit 37 and the fifth conduit 35 into the overflow outlet 34. As the first container 32 fills, the second fluid can leave the first container 32 through the container inlet 31, of the first container 32, and into the fourth conduit 25. Once in the fourth conduit 25, the second fluid can move from the fourth conduit 25 to the third conduit 23 and from the third conduit 23 into the outlet 13. According to another embodiment, any suitable mechanism can pump waste through the waste conduit 37. For example, gravity or a pump.

The combined effect of the pressure from the first pump 12 and the second pump 14 can push a blockage back into the chamber 16 and can cause a volume 50 of the fluid to enter the chamber 16. The volume 50 can collect between the formation 22 and the inside surface of the chamber 16. In some embodiments, the process illustrated in FIG. 2 and described above takes place in less or equal to about 25 seconds, about 45 seconds, or about 60 seconds.

FIG. 3 shows a later stage of the particle collection system 70 after detection of a blockage. The volume 50 and the material causing the blockage can exit the chamber 16. A sixth conduit 60 can extend from the chamber 16 to the fourth two-way valve 36. The sixth conduit 60 can extend from anywhere along the chamber 16. For example, the sixth conduit 60 can extend from the chamber 16 at an opening located at the bottom of the formation 22. In some embodiments, the sixth conduit 60 is cylindrical and has a large diameter as compared to the other conduits. The sixth conduit 60 can be larger than the diameter of the fourth conduit 25 by a factor of at least 1.25, 1.5, 1.75, 2, or 3. For example, the sixth conduit 60 may have a diameter greater than or equal to 1.6 mm.

The third two-way valve 30 can switch so that the first port 77 of the third two-way valve 30 can be open and the second port 78 of the third two-way valve 30 can be closed. The fourth two-way valve 36 can switch so that the first port 81 of the fourth two-way valve 36 can be closed and the second port 82 of the fourth two-way valve 36 can be open. The second port 82 of the fourth two-way valve 36 can connect with the waste conduit 37 which extends to the second container 38 via the second pump 14.

The second pump 14 can pump in the second direction and at an increased speed. The speed of the second pump 14 can be greater than or equal to 40 rpm, for example. The increased speed of the second pump 14 can cause volume 50 to exit the chamber 16. The volume 50 can enter the waste container 38 through the sixth conduit 60 and the waste conduit 37.

The first pump 12 can pump fluid from the third container 11. The second two-way valve 24 can switch to prevent the fluid from flowing to the particle collection device 1 and instead direct it to flow through the second conduit 40. The fluid from the third container 11 can move through the second conduit 40 into the fourth conduit 25. The second pump 14 can pump the fluid from the second conduit 40 to the fourth conduit 25. In some embodiments, the process illustrated in FIG. 3 and described above takes place in less or equal to about 25 seconds, about 45 seconds, or about 60 seconds. At the completion of this process, the particle collection system 70 can return to the state shown in FIG. 1.

Figure 4:
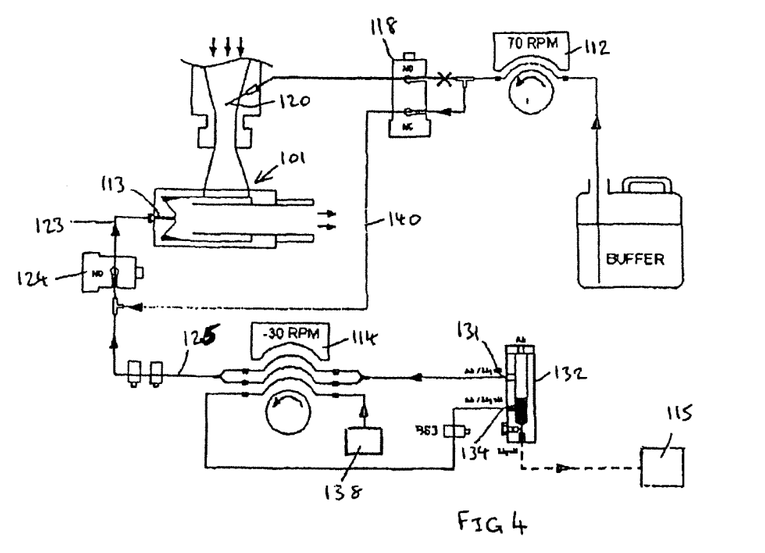
FIG. 4 is a schematic of another embodiment of a particle collection system at a preliminary stage of blockage clearance.
Figure 5:
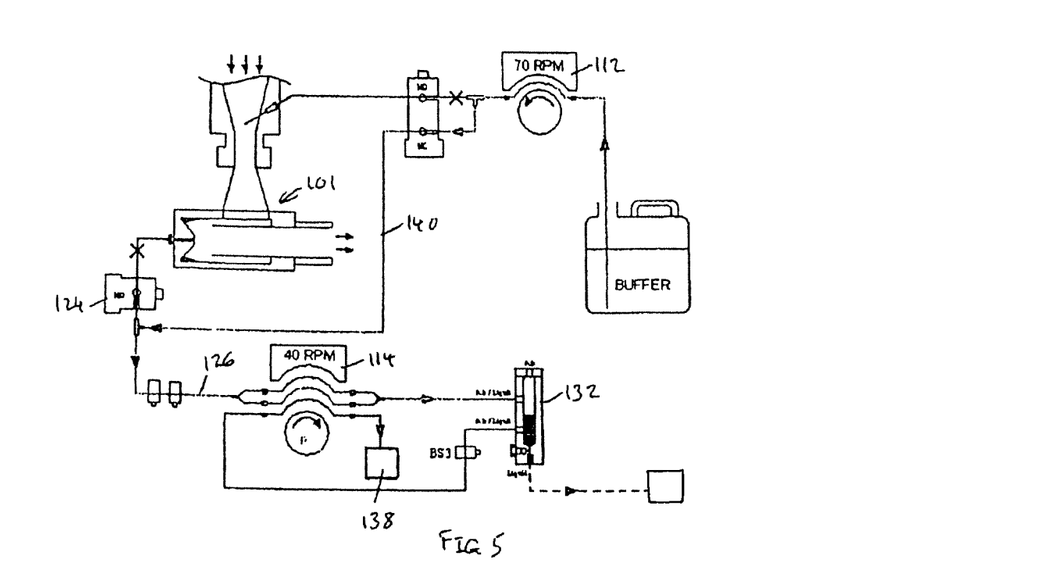
FIG. 5 is a schematic of the another embodiment of the particle collection system at a intermediate stage of blockage clearance.
Figure 6:
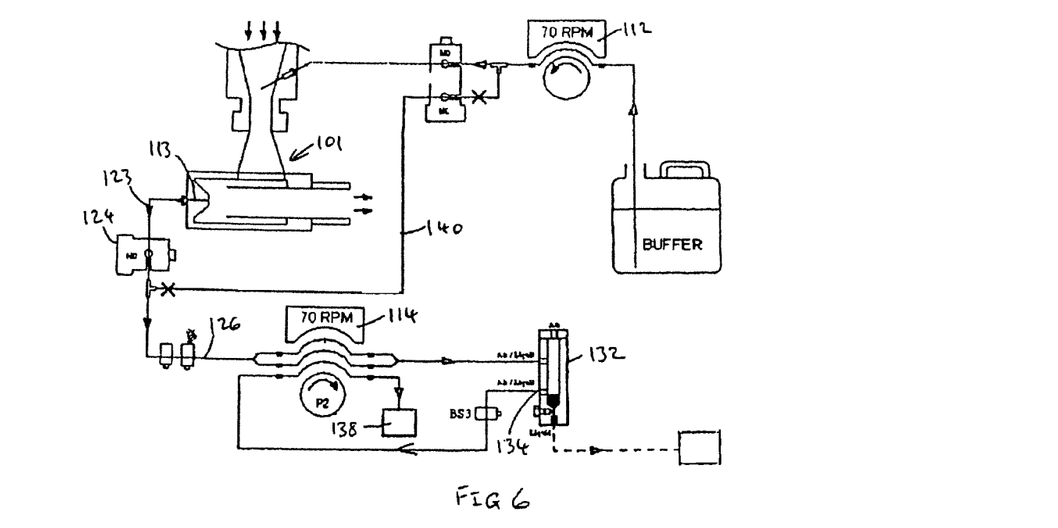
FIG. 6 is a schematic of the another embodiment of the particle collection system at a later stage of blockage clearance.
Figure 7:
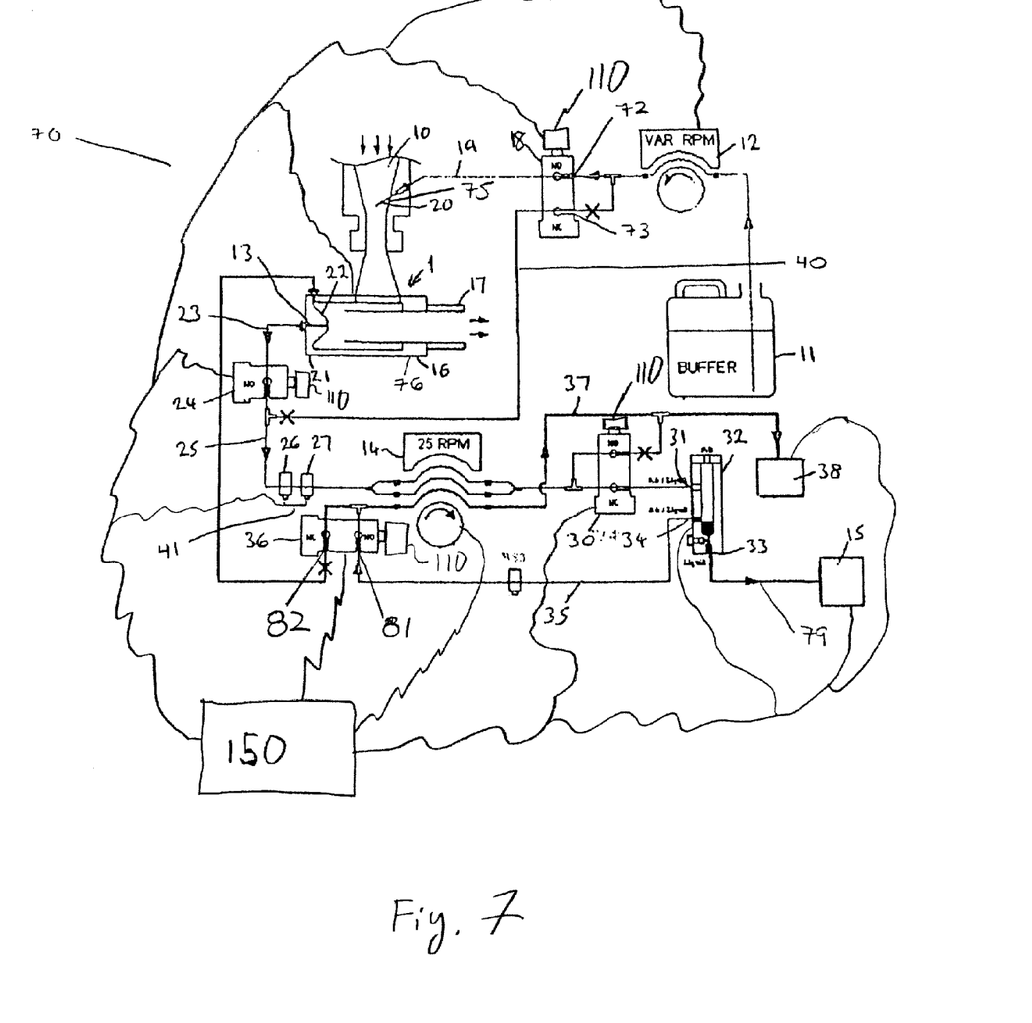
FIG. 7 is a schematic of another embodiment of the particle collection system.
Figure 8:
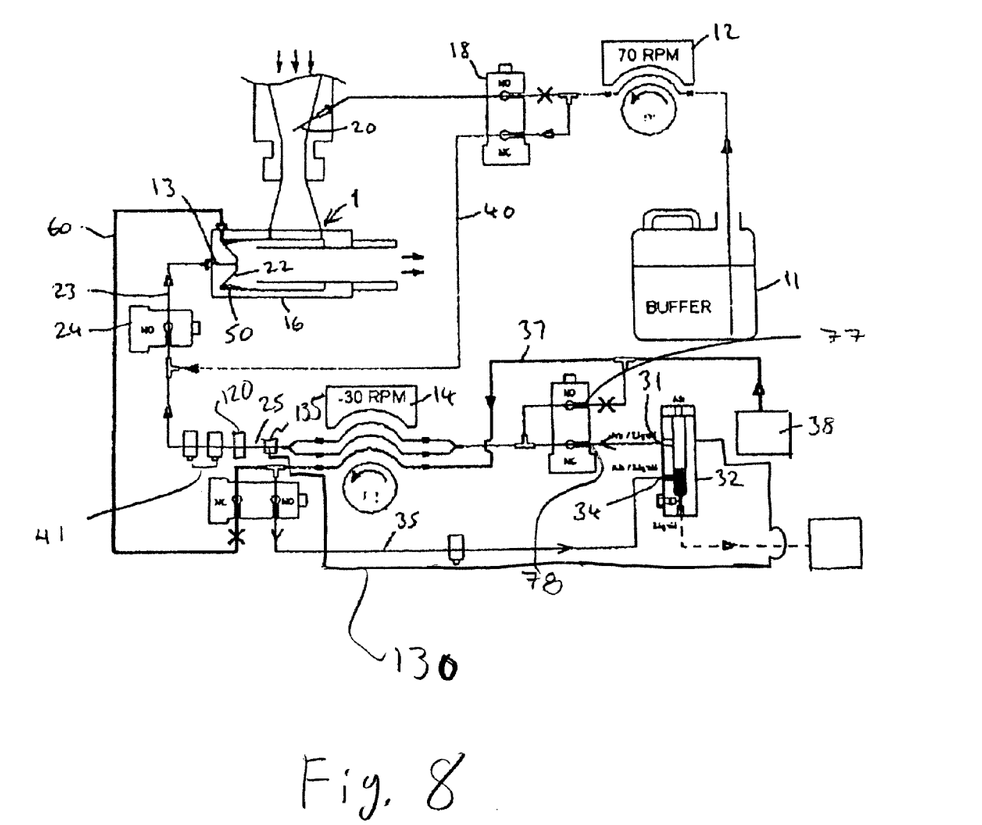
FIG. 8 is a schematic of another embodiment of the particle collection system.

FIGS. 4, 5, and 6 show another embodiment of the particle collection system 170. The particle collection system 170 is similar to the particle collection system 70, except the particle collection system 170 has no sixth conduit 60 and only contains two, two-way valves 118, 124. A blockage can be removed by the third conduit 123. The third conduit 123 can be any suitable shape, including, for example, cylindrical.

FIG. 4 shows a preliminary stage of the particle collection system 170 after detection of a blockage. The speed of the first pump 112 and the second pump 114 can increase. For example, the speed of the first pump 112 can increase to a speed of greater than or equal to 70 rpm, and the speed of the second pump 114 can increase to a speed of greater than or equal to 30 rpm. Alternatively, only one of the two pumps can increase in speed. The first pump 112 pumps in the first direction, and the second pump 114 pumps in the second direction.

The first pump 12 can connect to the first two-way valve 118. The first two-way valve 118 can have a first port 172 and a second port 173. The first two-way valve 118 can switch so that the second port 173 of the first-two way valve 118 can be open and the first port 172 of the first two-way valve 118 can be closed. Similar to the embodiment shown in FIG. 2, the closure of the first port 172 of the first two-way valve 118 can disconnect the first pump 112 from the needle 120. The opening of the second port 173 of the first two-way valve 118 can allow the first pump 112 to pump the fluid from the third container 111 to the second conduit 140, from the second conduit 140 to the second two-way valve 124, and from the second two-way valve 124 to the outlet 113.

When the second pump 114 pumps in the second direction, the second pump 114 can pump the second fluid from the second container 138 into the overflow outlet 134. As the first container 134 fills, the second fluid can exit through the container inlet 131 and can move through the fourth conduit 125 to the third conduit 123 and from the third conduit 123 to the outlet 113.

In some embodiments, the process illustrated in FIG. 4 and described above takes place in less or equal to about 15 seconds, about 25 seconds, about 45 seconds, or about 60 seconds. A blockage can be removed from within or around the outlet 113, from within the third conduit 123, and/or from within the fourth conduit 125.

FIG. 5 shows an intermediate stage of the particle collection system 170 after detection of a blockage. The second pump 114 can pump in the first direction, and the second two-way valve 124 can switch. The speed of the second pump 114 may or may not increase from the increased speed of the embodiment shown in FIG. 4. Switching the second two-way valve 124 can prevent the fluid from entering the particle collection device 101 so that the second pump 114 receives a flow of fluid from the first pump 112 via the second conduit 140 and the fourth conduit 125

The first pump 112 can pump the fluid from the third container 111 into the second conduit 140 and from the second conduit 140 to the fourth conduit 125. Any remaining blockage in the fourth conduit 125 can be pumped by the second pump 114 to the first container 132 and from the first container 132 to the second container 138. In some embodiments, the process illustrated in FIG. 5 and described above takes place in less or equal to about 15 seconds, about 25 seconds, about 45 seconds, or about 60 seconds.

FIG. 6 shows a later stage of the particle collection system 170 after detection of a blockage. The second two-way valve 124 can be switched. The first pump 112 and the second pump 114 each can operate in their respective first directions. The first pump 112 and the second pump 114 can operate at an increased speed. In some embodiments, both the first pump 112 and the second pump 114 can operate at an increased speed, or only one or neither can operate at an increased speed so that a larger amount of fluid is sprayed into the particle collection device 101 to wash out any remaining blockage. In some embodiments, the first pump 112 and second pump 114 operate at a speed greater than or equal to 70 rpm. The fluid pumped from the third container 111 can be pumped by the second pump 114 through the third conduit 123, from the third conduit 123 through the fourth conduit 125, and from the fourth conduit 125 into the first container 132. Fluid entering the first container 132 can exit the first container 132 through the overflow outlet 134 and can be pumped by the second pump 114 into the second container 138. In some embodiments, the process illustrated in FIG. 6 and described above takes place in less or equal to about 15 seconds, about 25 seconds, about 45 seconds, or about 60 seconds. After this, the particle collection system 170 returns to its normal operating mode.

Some exemplary scenarios detailing use of some embodiments will now be described.

With reference first to FIG. 1, a system includes a particle collection device 1 having a particle inlet 10. A sample collection solution, which can be a buffer solution from a third container 11 is supplied by a first pump 12 to the particle collection device 1 and collected samples are removed via an outlet 13 utilizing a second pump 14, and are supplied to an analysis unit 15.

The particle collection device 1 has a generally cylindrical chamber 16 (a collection chamber, which can contain a first fluid containing particles collected with the particle collection device) oriented horizontally (although alternative orientations are possible) with a particle inlet 10 opening into the chamber 16 tangentially so that air may be given a swirling motion about an axis of the chamber 16. In some embodiments, the particle collection device 1 is connected to a blower or impeller or the like at its particle inlet 10 or at a first outlet 17, or both, so that air is drawn through the particle collection device 1. The buffer solution is pumped from the third container 11 by the first pump 12 to an inlet of a two-way valve 18, which may connect via a first conduit 19 to a needle 20 projecting into the particle inlet 10, so that the buffer solution enters the chamber 16 with the air and any airborne particles. Referring to FIG. 1, the first portion 21 of the chamber 16 is closed and has a formation 22 projecting axially, up which flows the mixture of buffer solution and entrapped particles. The outlet 13 is provided by a narrow axial bore of, in an exemplary embodiment, about 0.8 mm in diameter opening at the top of the formation 22.

The outlet 13 connects via a first flow path, which in an exemplary embodiment can include the outlet 13 and a third conduit 23 (in an exemplary embodiment, about 0.5 mm internal diameter and part of a first flow path) to a second two-way valve 24, which can connect to a second length of fourth conduit 25 extending to the second pump 14. A detector 41 adapted to detect a change in a flow rate of fluid passing through the conduit indicative of a blockage at the first flow path is present, which, in the exemplary embodiment shown, comprises two bubble sensors 26 and 27 mounted at spaced locations along a first flow path, fourth conduit 25, to detect passage of air bubbles in the tubing.

Initially, during operation of the particle collection device 1 to obtain samples, the second pump 14 can be rotated at a relatively low speed of about 25 rpm in a forward direction to draw the buffer and particle mixture from the outlet 13 along the fourth conduit 25. A port of the second pump 14 connects with a third two-way valve 30, which normally connects the second pump 14 to a container inlet 31 of a first container 32. The first container 32 has a container outlet 33 at its lower end, which is open to allow flow from the first container 32 to the analysis unit 15. The rate of flow from the container outlet 33 can be regulated to be suitable for the particular analysis unit 15 used. The first container 32 can have an overflow outlet 34 between the container inlet 31 and the container outlet 33 so that, if solution should enter the first container 32 at a higher rate than is discharged through the container outlet 33, it would flow out of the overflow outlet 34. The overflow outlet 34 connects via a fifth conduit 35 to a fourth two-way valve 36, which, in the exemplary embodiment depicted in FIG. 1, connects to a waste conduit 37 and extends via the second pump 14 so that the waste solution is pumped into a second container 38. In operation, the buffer solution containing the collected particles in suspension can be drawn from the particle collection device 1 to the analysis unit 15 for detection and analysis.

If a blockage should occur in or around the outlet 13 of the particle collection device 1 or its associated conduit 23 or 25, this blockage would stop and/or reduce the flow along the fourth conduit 25 extending past the two bubble sensors 26 and 27. Flow rate along the fourth conduit 25 utilizing the embodiment depicted in the figures can be measured based on the time taken by a bubble to flow between the two sensors 26 and 27. If this time should increase above a predetermined value, such as 150%, this is taken as indicating a blockage. Further, a complete blockage would prevent any flow along the fourth conduit 25, so the absence of any output from the bubble sensors 26 and 27 for a predetermined time, such as 10 second is also taken as indicating the presence of a blockage. When a blockage is detected, the system starts an automatic unblock procedure, as will now be described.

First, as shown in FIG. 2, the first two-way valve 18 is switched to disconnect the first pump 12 from a nozzle 20 and instead connect the pump to a second conduit 40, a flow path, extending to the second two-way valve 24. This valve 24 switches to allow buffer solution to flow from the first pump 12 to the outlet 13 of the particle collection device 1. At the same time, the speed of the first pump 12 is increased to about 70 rpm, up from its previous variable speed, which can be controlled to provide a substantially constant outlet compensated for varying environmental conditions.

In this scenario, the second pump 14 is reversed and its speed increased to around 30 rpm. In this way, waste solution from the second container 38 is pumped by the second pump 14 along a waste conduit 37 and a fifth conduit 35 into the overflow outlet 34 of the first container 32. The first container 32 fills so that fluid can be drawn out from its container inlet 31 to flow along conduits 25 and 23 to the outlet 13 along with the buffer solution direct from the third container 11. The combined effect of the pressure from the two pumps 12 and 14 forms an unblocking fluid which can be a combination of the buffer solution and the sample fluid from the particle collection device 1 containing particles which travels in a direction opposite to the sample flow down the first flow path and acts to push the blockage back into the chamber 16 and causes a volume 50 of buffer solution to enter the particle collection device 1 to help break down and disperse the blockage material. The volume 50 collects in the annular corner between the formation 22 and the inside cylindrical surface of the chamber 16. This takes place for about 25 seconds.

The next stage, shown in FIG. 3, involves removal of this volume 50 of solution with the blockage material. A sixth conduit 60 (in some embodiments having an internal diameter of about 1.6 mm) extends from the chamber 16 where it opens into the corner at the bottom of the formation 22. The opposite end of the sixth conduit 60 connects with the fourth two-way valve 36 and is normally closed by this valve but is opened during this removal stage. A port of the two-way valve 36 connects with the waste conduit 37, which extends to the waste container 38 via the second pump 14. The second pump 14 is now driven forwards at an increased speed of about 40 rpm so that the volume 50 is drawn away to the second container 38 via the sixth conduit 60 and the waste line 37. The pump 12 continues to pump buffer solution from the third container 11 but the second two-way valve 24 is now switched to prevent the buffer flowing to the particle collection device 1 and instead direct it to flow via second conduit 40 along the fourth conduit 25 to the second pump 14 to help clear any material in this conduit. This takes place for about 25 seconds in this exemplary scenario. After this process has been completed, the system returns to its normal operating mode.

In some embodiments, the system does not employ a sixth conduit 60 of the type depicted in FIGS. 1 to 3, as can be seen in the exemplary embodiment shown in FIGS. 4 to 6, where equivalent components to those in FIGS. 1 to 3 are given the same numerals with the addition of 100. The system of FIGS. 4-6 has only two two-way valves 118 and 124, where blockage material is removed via the outlet line 123.

FIG. 4 depicts the initial stage after detection of a blockage. After a blockage is detected, the pump 112 can be driven at high speed, around 70 rpm, in a reverse direction from its normal operation. The first two-way valve 118 can be switched to disconnect the first pump 112 from the nozzle 120 and instead to supply the buffer solution along the second conduit 140 to the second two-way valve 124. This valve 124 can be set such that the buffer solution flows to the inlet 113 via the third conduit 123. The second pump 114 also can be reversed and driven at a higher than normal speed of around 30 rpm. This causes waste solution in the second container 138 to be pumped into the overflow outlet 134 of the first container 132. As the first container 132 fills, the solution can flow out of the container inlet 131 and back along conduit 126, via the second pump 114 and the two-way valve 124 to add to the solution pumped to the outlet 113 from the first pump 112. This initial flushing takes place for about 15 seconds and can be effective to push out blockages in or around the outlet 113, or in its associated conduits 123, 126.

In the next stage, as shown in FIG. 5, the direction of rotation of the second pump 114 can be reversed so that it rotates in the normal direction. The second two-way valve 124 can be switched to prevent flow to or from the particle collection device 101 so that the second pump 114 receives a flow of clean buffer solution from the first pump 112 via conduits 140 and 126. Any remaining blockage material in conduit 126 can be flushed through via the first container 132 to the waste container 138. This stage can also take place for about 15 seconds.

The final stage, shown in FIG. 6 is to remove material from the particle collection device 101. This can be achieved by switching valve 124 to close conduit 140 and to open the path between the outlet 113 and the second pump 114. Both pumps 112 and 114 can be driven in their normal forward direction but at high speed, typically around 70 rpm so that a larger than usual amount of buffer solution is sprayed into the particle collection device 101 to wash out any remaining material. The solution can be drawn by the second pump 114 via conduits 123 and 126 into the first container 132 where it overflows to its container outlet 134 and is pumped to the second container 138 by the second pump 114. This can take place for about 15 seconds, after which the system switches to its normal operating mode.

In some embodiments, blockages in the system can be cleared automatically, without user intervention. In some embodiments, cyclone or other systems can be operated unattended for prolonged periods. Other systems other than cyclone systems can be utilized for particle separators. Some or all features disclosed herein can be used in other particle collection systems and/or in any other arrangement where blockage is a problem and/or where filters cannot be used/are not adequate.

As can be seen from the Figures, in an embodiment, there is an apparatus comprising a particle collection device 1 having a chamber 16 containing a first fluid and including an outlet 13, a first fluid distribution system adapted to direct the first fluid from the particle collection device 1 through the outlet 13 to flow along a first flow path 23 in a first flow direction, the first flow path 23 including the outlet 13, a detector 84 including sensors 26/27 adapted to detect a change in a flow rate of the first fluid directed in the first flow direction indicative of a blockage at the first flow path 23, wherein the apparatus is adapted to automatically direct unblocking fluid to flow along the first flow path 23 in a second flow direction opposite the first flow direction upon the detection of the change in the flow rate indicative of a blockage at the first flow path 23 to remove the blockage at the first flow path.

In another embodiment, the detector 41 comprises a flow rate meter selected from the group consisting of a variable area flow rate meter, an electromagnetic flow rate meter, a coriolis flow rate meter, a caliometric flow rate meter, a pitot tube flow rate meter, a differential pressure flow rate meter, a thermal conductivity flow rate meter, a vortex shedding flow rate meter, an ultrasonic flow rate meter, a turbine flow rate meter, an optical flow rate meter, and a rotary gear flow rate meter.

In another embodiment, there is an apparatus as disclosed above or below, wherein the unblocking fluid comprises the first fluid which has passed through the particle collection device and exited through outlet 13 and entered the first flow path 23. In another embodiment, the unblocking fluid comprises a buffer solution that has not passed through the collection chamber 16 of the particle collection device 1, having been routed around the particle collection device 1 via flow path 40.

In another embodiment, there is an apparatus wherein upon the detection of the change in the flow rate indicative of a blockage at the first flow path 23, the apparatus is adapted to reverse the direction of the first fluid flowing along the first flow path 23 to flow along the first flow path 23 in the second flow direction, the unblocking fluid comprising the first fluid flowing along the first flow path 23 in the second flow direction. In another embodiment, upon the detection of the change in the flow rate indicative of a blockage at the first flow path 23, the apparatus can be adapted to direct a second fluid to flow along the first flow path 23 in the second flow direction (e.g., in a direction from the second two-way valve 24 towards outlet 13), the unblocking fluid comprising the second fluid flowing along the first flow path 23 in the second flow direction.

In an exemplary embodiment, the pump 14 is a sample pump adapted to pump the first fluid containing the sample from the collection chamber 16 so that the first fluid flows along the first flow path (the first flow path including at least a portion of conduit 23). In an exemplary embodiment, the pump 12 is a sample collection solution supply pump adapted to pump sample collection solution from a supply of the sample collection solution 11 into the collection chamber 16 of the particle collection device 1. According to another embodiment, the pump 12 is a sample collection solution supply pump adapted to operate at a variable pump speed to pump the sample collection solution into the particle collection chamber 16 of the particle collection device 1.

According to one embodiment, the sixth conduit 60 is a waste outlet where the volume 50 is drawn from the cyclone chamber 16 (the particle collection chamber 16, when the device 1 is a cyclone—that is, in an embodiment, the particle collection device 1 is a cyclone separator device and the chamber 12 is a cyclone chamber of the cyclone separator device) through the waste outlet to a waste container 38.

It is noted that the various features disclosed and described herein can be combined together in any combination that will permit the present invention to be practiced. Also, an embodiment includes any device, method or system to implement the various methods, use steps, and exemplary usage scenarios disclosed herein. It is further noted that dimensions are provide herein by way of example only and not by way of limitation. In this regard, in some embodiments of the present invention, the dimensions may vary by plus or minus about 1% to about 100%, or even more. Also, in some embodiments of the invention, the dimensions are uniformly scaled up and/or scaled down.

The embodiments described above have been set forth herein for the purpose of illustration and are exemplary in nature unless otherwise explicitly stated. This description, however, should not be deemed to be a limitation on the scope of the embodiments. This is especially true with respect to various specific dimensions and regimes detailed herein. Various modifications, adaptations, and alternatives may occur to one skilled in the art without departing from the claimed concept.

What is claimed is:

1. A substance detection device, comprising:
   a chemical substance analyzer, including:
      an ion mobility spectrometer (IMS);
      a conduit; and
      a membrane, wherein the membrane extends across a cross-section of the conduit, wherein the membrane is positioned to have one side and an analysis side opposite the one side,
      wherein the substance detection device is adapted to direct a portion of a chemical substance to the one side through the conduit so that at least a portion of the chemical substance is transferred to the membrane by interacting with the one side of the membrane, wherein the membrane is adapted to diffuse at least a portion of the chemical substance transferred to the membrane through the membrane to the analysis side; and a particle separation apparatus, including:
a particle collection device having a collection chamber containing a first fluid and including an outlet, wherein the first fluid is a sample fluid containing particles collected by the particle collection device;
a first fluid distribution system adapted to direct the first fluid from the particle collection device through the outlet to flow along a first flow path in a first flow direction; and
a detector adapted to detect a change in a flow rate of the first fluid directed in the first flow direction indicative of a blockage at the first flow path, wherein
the apparatus is adapted to automatically direct an unblocking fluid to flow along the first flow path in a second flow direction opposite the first flow direction upon the detection of the change in the flow rate indicative of a blockage at the first flow path to remove the blockage at the first flow path, and
wherein the outlet is in fluid communication with the conduit such that particles directed through the outlet travel through the conduit and chemical substances which may be on those particles directed through the outlet are transferred to the membrane by interacting with the one side of the membrane.

2. An apparatus, comprising:
a particle collection device having a collection chamber containing a first fluid and including an outlet, wherein the first fluid is a sample fluid containing particles collected by the particle collection device;
a first fluid distribution system adapted to direct the first fluid from the particle collection device through the outlet to flow along a first flow path in a first flow direction;
a detector adapted to detect a change in a flow rate of the first fluid directed in the first flow direction indicative of a blockage at the first flow path, wherein
the apparatus is adapted to automatically direct an unblocking fluid to flow along the first flow path in a second flow direction opposite the first flow direction upon the detection of the change in the flow rate indicative of a blockage at the first flow path to remove the blockage at the first flow path.

3. The apparatus of claim 2, wherein the detector comprises a flow rate meter selected from the group consisting of a variable area flow rate meter, an electromagnetic flow rate meter, a coriolis flow rate meter, a caliometric flow rate meter, a pitot tube flow rate meter, a differential pressure flow rate meter, a thermal conductivity flow rate meter, a vortex shedding flow rate meter, an ultrasonic flow rate meter, a turbine flow rate meter, an optical flow rate meter, and a rotary gear flow rate meter.

4. The apparatus of claim 2, wherein the unblocking fluid comprises the first fluid which has passed through the collection chamber.

5. The apparatus of claim 2, wherein the unblocking fluid comprises a sample collection solution that has not passed through the collection chamber of the particle collection device.

6. The apparatus of claim 2, wherein upon the detection of the change in the flow rate indicative of a blockage at the first flow path, the apparatus is adapted to reverse the direction of the first fluid flowing along the first flow path to flow along the first flow path in the second flow direction, the unblocking fluid comprising the first fluid flowing along the first flow path in the second flow direction.

7. The apparatus of claim 2, wherein upon the detection of the change in the flow rate indicative of a blockage at the first flow path, the apparatus is adapted to direct a second fluid to flow along the first flow path in the second flow direction, the unblocking fluid comprising the second fluid flowing along the first flow path in the second flow direction.

8. The apparatus of claim 7, wherein upon the detection of the change in the flow rate indicative of a blockage at the first flow path, the apparatus is adapted to reverse the direction of the first fluid flowing along the first flow path to flow along the first flow path in the second flow direction, the unblocking fluid comprising (i) the first fluid flowing along the first flow path in the second flow direction, and (ii) the second fluid flowing along the first flow path in the second flow direction.

9. The apparatus of claim 8, wherein the second fluid comprises a sample collection solution that has not passed through the collection chamber of the particle collection device.

10. The apparatus of claim 7, wherein the apparatus includes a sample collection solution supply system adapted to supply sample collection solution to the collection chamber of the particle collection device in an absence of the detection of the change in the flow rate indicative of a blockage at the first flow path, wherein the apparatus is adapted to, upon the detection of the change in the flow rate indicative of a blockage at the first flow path, supply sample collection solution that has not passed through the collection chamber of the particle collection device as the second fluid and direct the second fluid to flow along the first flow path in the second flow direction.

11. The apparatus of claim 10, wherein:
the first fluid distribution system includes a first pump adapted to pump the first fluid flowing along the first flow path in the first direction;
the sample collection solution supply system includes a second pump adapted to pump the sample collection solution from a supply of the sample collection solution into the collection chamber of the particle collection device;
the apparatus is adapted to reverse a direction of the first fluid flowing through the first pump to pump the first fluid along the first flow path in the second flow direction; and
the apparatus is adapted to maintain a direction of the sample collection solution flowing through the second pump while directing sample collection solution which has not passed through the collection chamber of the particle collection device to a location, with respect to a partial fluid circuit that includes the outlet and the first pump, between the outlet and the first pump, wherein the sample collection solution that has not passed through the collection chamber of the particle collection device, being the second fluid, combines with the first fluid to form the unblocking fluid and to flow along the first flow path in the second flow direction.

12. The apparatus of claim 10, wherein:
the first fluid distribution system includes a sample pump adapted to operate at a first pump speed to pump the first fluid flowing along the first flow path in the first direction;
the sample collection solution supply system includes a sample collection solution supply pump adapted to operate at a variable pump speed to pump the sample collection solution into the particle collection device;

the apparatus is adapted to reverse a direction of the first fluid flowing through the sample pump and increase the speed of the sample pump to a second pump speed, to pump the first fluid along the first flow path in the second flow direction, the absolute value of the second pump speed being greater that the absolute value of the first pump speed; and the apparatus is adapted to maintain a direction of the sample collection solution flowing through the sample collection solution supply pump while increasing the speed of the sample collection solution supply pump over the variable pump speed while directing sample collection solution that has not passed through the collection chamber of the particle collection device to a location, with respect to a partial fluid circuit that includes the outlet and the first pump, between the outlet and the first pump, wherein the sample collection solution that has not passed through the collection chamber of the particle collection device, as the second fluid, combines with the first fluid to form the unblocking fluid and to flow along the first flow path in the second flow direction.

13. The apparatus of claim 2, wherein the apparatus is adapted to determine that the detector has detected a change in the flow rate of the first fluid directed in the first direction indicative of a blockage at the first flow path when at least one of (i) a flow rate of the first fluid flowing in the first flow path decreases by a predetermined regime, and (ii) no movement of the first fluid between two locations in the first flow path is detected.

14. The apparatus of claim 10, wherein the apparatus includes a sample dispensing container including an overflow outlet, a supply of the sample collection solution, a waste container, a sample pump, and a sample collection solution supply pump adapted to pump sample collection solution from the supply of the sample collection solution, wherein the first fluid is a sample from the particle collection device which includes particles collected in the particle collection device, wherein the apparatus is adapted to direct, prior to detection of the change in the flow rate indicative of a blockage at the first flow path, the first fluid into the sample dispensing container, and wherein upon the detection of the change in the flow rate indicative of a blockage at the first flow path, the apparatus is adapted to:

disconnect the supply of the sample collection solution to the collection chamber of the particle collection device and to connect the supply of the sample collection solution to the first flow path to allow sample collection solution to flow from the supply of the sample collection solution, while bypassing the collection chamber of the particle collection device, to the outlet of the particle collection device;

increase a speed of the sample collection solution supply pump adapted to pump sample collection solution from the supply of the sample collection solution;

reverse the direction of the sample pump and increasing the speed of the sample pump so that the speed of the sample pump has an absolute value that is greater than an absolute value of the sample pump speed just prior to the detection of the change in the flow rate indicative of a blockage at the first flow path; and pump, using the sample pump operating in the reversed direction and at the increased speed, waste solution from the waste container of the apparatus into the overflow outlet of the sample dispensing container such that sample stored in the sample dispensing container is forced out of the sample dispensing container and flows towards the outlet of the collection chamber so that the first fluid flowing along the first flow path flows along the first flow path in the second flow direction, wherein the first fluid and the second fluid combine to form the unblocking fluid flowing along the first flow path in the second flow direction.

15. A method of clearing a blockage, comprising:

during a first temporal period, obtaining the apparatus of claim 10, the apparatus further including a sample dispensing container including an overflow outlet, a supply of the sample collection solution, a waste container, a sample pump, and a sample collection solution supply pump adapted to pump sample collection solution from the supply of the sample collection solution, wherein the first fluid is a sample from the particle collection device which includes particles collected in the particle collection device;

during the first temporal period, directing the first fluid into the sample dispensing container;

during the first temporal period, detecting, using the detector, a change in a phenomenon indicative of a blockage at the first flow path;

during the first temporal period, disconnecting a supply of the sample collection solution from the particle collection device and connecting the supply of the sample collection solution to the first flow path and directing the sample collection solution to flow from the supply of the sample collection solution while bypassing the collection chamber of the particle collection device to the outlet of the particle collection device;

during a second temporal period after the first temporal period, increasing a speed of the sample collection solution supply pump to a speed greater than a speed of the sample collection solution supply pump during the first temporal period to pump sample collection solution from the supply of the sample collection solution;

during the second temporal period, reversing the direction of the sample pump from a direction of the sample pump during the first temporal period and increasing the speed of the sample pump so that the speed of the sample pump has an absolute value that is greater than an absolute value of the sample pump speed during the first temporal period;

during the second temporal period, pumping, using the sample pump operating at the reversed direction and increased speed, waste solution from the waste container of the apparatus into the overflow outlet of the sample dispensing container, such that sample stored in the sample dispensing container is forced out of the sample dispensing container and flows towards the outlet of the collection chamber so that the first fluid flowing along the first flow path flows along the first flow path in the second flow direction, wherein the first fluid and the second fluid combine to form the unblocking fluid flowing along the first flow path in the second flow direction.

16. The method of claim 15, wherein the particle collection device is a cyclone separator device, the method further comprising, during the second temporal period, utilizing the sample pump and the sample collection solution supply pump to push a blockage material at the first flow path causing a blockage at the first flow path into the particle collection device such that a volume comprising sample collection solution and blockage material collects in a cyclone chamber of the cyclone separator device.

17. The method of claim 16, further comprising:
during a third temporal period after the second temporal period, opening a waste outlet connected to the cyclone chamber;
during the third temporal period, reversing the direction of the sample pump from the direction of the sample pump during the second temporal period and increasing the speed of the sample pump so that the speed of the sample pump has an absolute value that is greater than an absolute value of the sample pump speed during the second temporal period; and
during the third temporal period, sucking the volume from the cyclone chamber through waste outlet to the waste container utilizing a suction generated by the sample pump operating at the reversed direction of the sample pump reversed the second time.

18. The method of claim 17, further comprising:
during the third temporal period, halting further sample collection solution flow from the supply of the sample collection solution bypassing the collection chamber of the particle collection device to the outlet of the particle collection device; and
during the third temporal period, directing the sample collection solution to flow from the supply of the sample collection solution into the sample pump while bypassing the collection chamber of the particle collection device so as to clear material in a flow path extending from the first flow path to at least one of the sample pump, the waste container, and the sample dispensing container.

19. The method of claim 16, further comprising:
during a third temporal period after the second temporal period, reversing the direction of the sample pump from the direction of the sample pump during the second temporal period and increasing the speed of the sample pump so that the speed of the sample pump has an absolute value that is greater than an absolute value of the sample pump speed during the second temporal period;
during the third temporal period, preventing flow through the first flow path in the first flow direction and the second flow direction; and
during the third temporal period, directing the sample collection solution to flow from the supply of the sample collection solution into the sample pump while bypassing the collection chamber of the particle collection device while operating the sample collection solution supply pump at the increased speed so as to clear material in a flow path extending from the first flow path to at least one of the sample pump, the waste container, and the sample dispensing container.

20. The method of claim 19, further comprising:
during a fourth temporal period after the third temporal period, re-enabling flow through the first flow path in the first flow direction and the second flow direction;
during the fourth temporal period, increasing the speed of the sample pump above the speed of the sample pump during the third temporal period; and
during the fourth temporal period, halting the sample collection solution from flowing from the supply of the sample collection solution into the sample pump while bypassing the collection chamber of the particle collection device, and operating the sample collection solution supply pump at the increased speed so as to flush the volume from the cyclone chamber through the outlet to the waste container.

21. An apparatus, comprising:
a particle collection device containing a first fluid and including an outlet;
a first fluid distribution system adapted to direct the first fluid from the particle collection device through the outlet to flow along a first flow path in a first flow direction, the first flow path including the outlet;
a detector adapted to detect a change in a flow rate of the first fluid directed in the first flow direction indicative of a blockage at the first flow path; and
an unblocking means for automatically unblocking a blockage at the first flow path.

22. A method of operating a particle collection apparatus, comprising:
during a first temporal period, collecting particles utilizing a cyclone particle collector in a first fluid, the first fluid being located in a collection chamber of the cyclone particle collector including an outlet;
during the first temporal period, directing the first fluid through the outlet to flow along a first flow path in a first flow direction, the first flow path including the outlet;
during the first temporal period, automatically detecting a change in a flow rate of the first fluid directed in the first flow direction indicative of a blockage at the first flow path;
during a second temporal period after the first temporal period, automatically direct unblocking fluid to flow along the first flow path in a second flow direction opposite the first flow direction upon the detection of the change in the flow rate indicative of a blockage at the first flow path to remove the blockage at the first flow path; and
during a third temporal period after the second temporal period, automatically directing the first fluid through the outlet to flow along the first flow path in the first flow direction.

23. An apparatus, comprising:
a particle collection device containing a first fluid and including an outlet;
a first pump adapted to pump the first fluid from the particle collection device through the outlet in a first direction along a first flow path in fluid communication with the outlet;
a detector adapted to detect a change in a flow rate of the first fluid pumped in the first direction from the outlet indicative of a blockage at the first flow path, wherein
the apparatus is adapted to change the direction along the first flow path of the first fluid upon the detection of the change in the flow rate indicative of a blockage at the first flow path.

* * * * *